United States Patent
Kamepalli et al.

(10) Patent No.: US 6,989,457 B2
(45) Date of Patent: Jan. 24, 2006

(54) CHEMICAL VAPOR DEPOSITION PRECURSORS FOR DEPOSITION OF TANTALUM-BASED MATERIALS

(75) Inventors: Smuruthi Kamepalli, Rochester, MI (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 137 days.

(21) Appl. No.: 10/345,616

(22) Filed: Jan. 16, 2003

(65) Prior Publication Data

US 2004/0142555 A1 Jul. 22, 2004

(51) Int. Cl.
 C07F 9/00  (2006.01)
 H01L 21/44 (2006.01)
 B05D 1/02  (2006.01)
 C23C 14/26 (2006.01)

(52) U.S. Cl. .............. 556/11; 556/12; 556/43; 438/685; 427/427; 427/587

(58) Field of Classification Search ............. 556/11, 556/12, 43; 438/685; 427/427, 587
See application file for complete search history.

(56) References Cited

U.S. PATENT DOCUMENTS 6,015,917 A * 1/2000 Bhandari et al. ............ 556/12
6,399,532 B1   6/2002 Dorer et al.

* cited by examiner

*Primary Examiner*—Porfirio Nazario-Gonzalez
(74) *Attorney, Agent, or Firm*—Margaret Chappuis; Steven J. Hultquist; Tristan A. Fuierer

(57) ABSTRACT

Tantalum precursors suitable for chemical vapor deposition of tantalum-containing material, e.g., tantalum, TaN, TaSiN, etc., on substrates. The tantalum precursors are substituted cyclopentadienyl tantalum compounds. In one aspect of the invention, such compounds are silylated to constitute tantalum/silicon source reagents. The precursors of the invention are advantageously employed in semiconductor manufacturing applications to form diffusion barriers in connection with copper metallization of the semiconductor device structure.

58 Claims, 1 Drawing Sheet

CHEMICAL VAPOR DEPOSITION PRECURSORS FOR DEPOSITION OF TANTALUM-BASED MATERIALS

FIELD OF THE INVENTION

The present invention relates to the deposition of tantalum-based materials, and to precursor compositions having utility for chemical vapor deposition of such materials on substrates, e.g., in the manufacture of semiconductor products.

DESCRIPTION OF THE RELATED ART

The ability to deposit conformal tantalum-based diffusion barriers is critical to the widespread adoption of copper metallization technology in semiconductor manufacturing operations.

Although the use of physical vapor deposition (PVD) is commonly employed for forming Ta, TaN and TaSiN thin film diffusion barrier layers, there are substantial and unresolved issues concerning the suitability of PVD processes for deposition at dimensions below 0.13 μm, as is required in the fabrication of future high performance microelectronic devices.

Considering chemical vapor deposition as a potential deposition technique, currently available organometallic tantalum precursors suffer from the incorporation of high levels of carbon, nitrogen and oxygen in the deposited tantalum film, which render the deposited tantalum-based material unsatisfactory for use as a diffusion barrier for copper metallization.

Accordingly, there is a compelling need in the art for suitable tantalum precursors for forming diffusion barriers in connection with copper metallization.

SUMMARY OF THE INVENTION

The present invention relates to the deposition of tantalum-based materials, and to precursor compositions having utility for the chemical vapor deposition of such materials on substrates, e.g., in the manufacture of semiconductor products.

In one aspect, the invention relates to a compound of the formula:

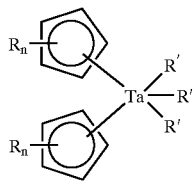

(I)

wherein:

n is an integer having a value of from 1 to 5;

each R can be the same or different and each is independently selected from the group consisting of Deuterium (hereinafter referred to as "D"), H, $CH_3$, $C_2H_5$, i-$C_3H_7$, $C_4H_9$ and $Si(R")_3$ wherein each R" is independently selected from H and $C_1$–$C_4$ alkyl; and each of R' can be the same or different and each is independently selected from the group consisting of D, H, $C_1$–$C_4$ alkyl, and $Si(R")_3$ wherein each R" is independently selected from H and $C_1$–$C_4$ alkyl;

with the proviso that each of the R and R' groups are not simultaneously all H.

Another aspect of the invention relates to specific preferred compounds of the above formula (I), viz.,

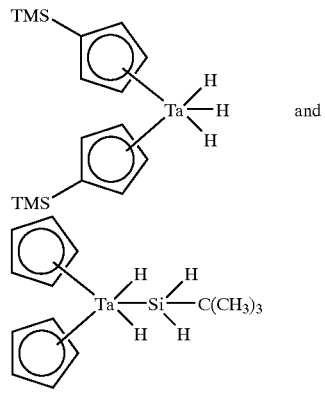

and

In another aspect, the invention relates to a method of forming a tantalum-containing material on a substrate, comprising contacting the substrate with a vapor of a tantalum precursor under chemical vapor deposition conditions, wherein the tantalum precursor comprises a compound of the above formula (I).

A further aspect of the invention relates to a method of synthesizing a cyclopentadienyl tantalum compound of the formula $[(R)_nCp]_2Ta\ R'_3$ wherein:

n is an integer having a value of from 1 to 5;

each R can be the same or different and each is independently selected from the group consisting of D, H and $Si(R")_3$ wherein each R" is independently selected from H and $C_1$–$C_4$ alkyl; and each of R' can be the same or different and each is independently selected from the group consisting of H, $C_1$–$C_4$ alkyl, and $Si(R")_3$ wherein each R" is independently selected from H and $C_1$–$C_4$ alkyl;

with the proviso that each of the R and R' groups are not simultaneously all H;

such method comprising reacting tantalum pentachloride with cyclopentadienyllithium compound of the formula $[(R)_nCp]Li$ in a 1:2 ratio, and stepwise addition of sodium borohydride compound of the formula $NaBH_4$, to yield said cyclopentadienyl tantalum hydride or deuteride compound.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
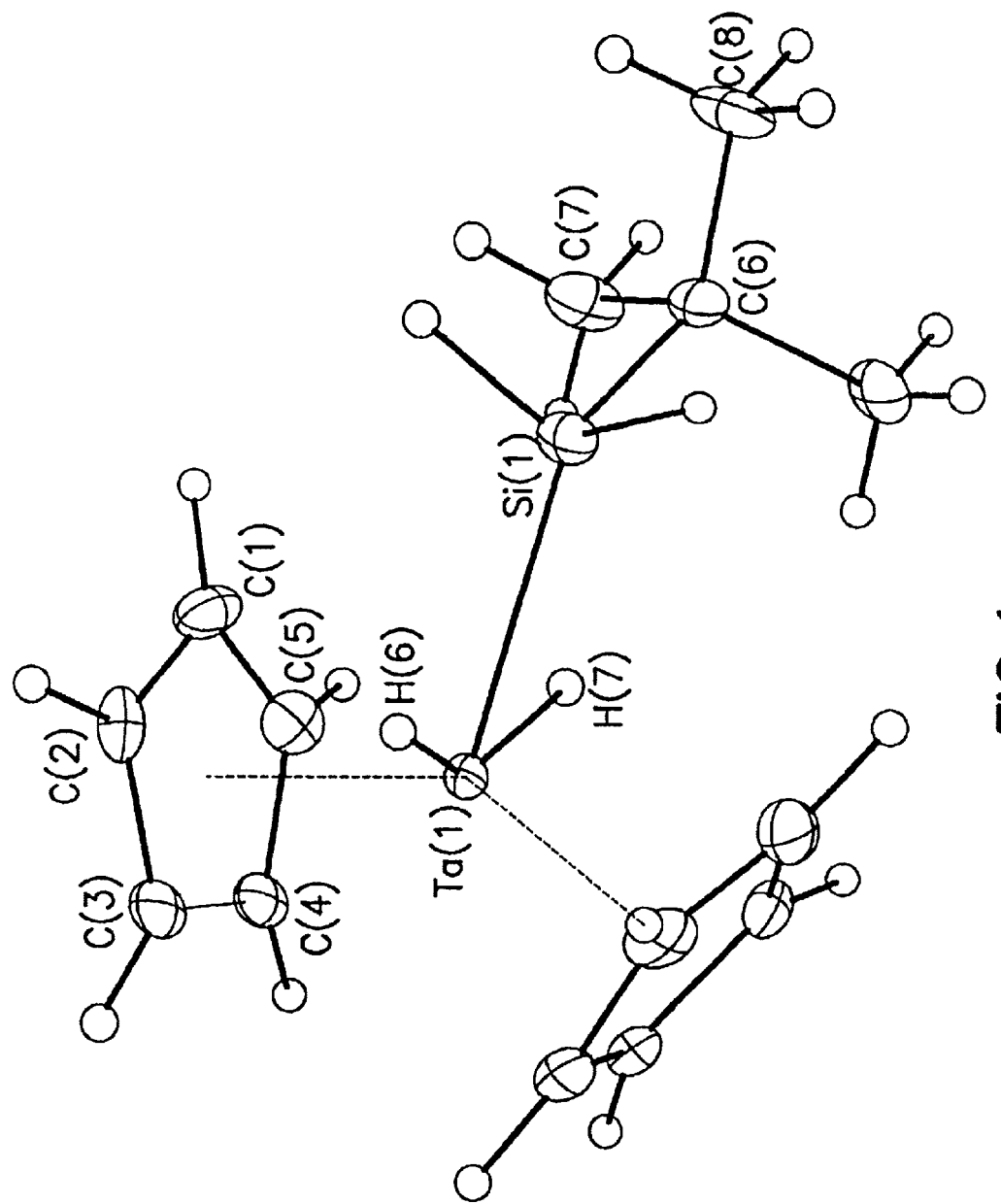
FIG. 1 is an ORTEP diagram of bis(cyclopentadienyl) dihydrido-t-butylsilyl tantalum.

The present invention is based on the discovery of novel cyclopentadienyl tantalum compounds that have surprising and unexpectedly superior utility for deposition of tantalum-based materials on substrates, e.g., as diffusion barrier layers in connection with copper metallization on such substrates.

The cyclopentadienyl tantalum compounds of the invention have the general formula (I):

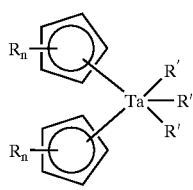

(I)

wherein:

n is an integer having a value of from 1 to 5;

each R can be the same or different and each is independently selected from the group consisting of D, H, $CH_3$, $C_2H_5$, i-$C_3H_7$, $C_4H_9$ and $Si(R'')_3$ wherein each R'' is independently selected from H and $C_1$–$C_4$ alkyl; and each of R' can be the same or different and each is independently selected from the group consisting of D, H, $C_1$–$C_4$ alkyl, and $Si(R'')_3$ wherein each R'' is independently selected from H and $C_1$–$C_4$ alkyl;

with the proviso that each of the R and R' groups are not simultaneously all H.

The compounds of the above general formula afford surprising and unexpected advantages over compounds such as bis(cyclopentadienyl)trihydridotantalum, in which the presence of hydrogen and cyclopentadienyl (Cp) moieties provide a facile route for metal center reduction and protonation of the Cp moieties to form stable CpH compounds and leaving behind pure tantalum films under appropriate process conditions. While superficially appearing highly advantageous in application to chemical vapor deposition usage, such compound, bis(cyclopentadienyl)trihydridotantalum, in fact has the severe deficiency that it decomposes immediately after melting to eliminate H2 and form Cp2TaH, which thereupon polymerizes. The polymer product of course is wholly unsuitable for CVD application, and the polymeric deposit on the surfaces of the vaporization chamber and associated vapor flow lines renders the CVD process system equipment incapable of operation and susceptible to dangerous over-pressurization as a result of occlusion of vapor flow passages of the system with the deposited polymeric residue.

Thus, bis(cyclopentadienyl)trihydridotantalum is not useful as a precursor for CVD formation of Ta and Ta-based films on substrates.

Such deficiency of Cp2TaH3 is overcome by the compounds of the present invention, which are stable under volatilization conditions and evidence good transport properties in application to CVD processes.

The compounds of the present invention therefore may be volatilized to form precursor vapor for contacting under CVD process conditions with substrates to form tantalum- and tantalum containing films thereon. The substrate for such purpose can comprise a semiconductor substrate, on which the deposited tantalum can be converted to tantalum nitride by CVD conducted in a nitrogen atmosphere, or by post-deposition nitridation of the deposited tantalum.

In a further embodiment, the tantalum precursors of the invention can be employed to form tantalum silicon nitride films, e.g., TaSiN, by concurrent chemical vapor deposition of silicon from a suitable silicon source reagent compound, and with the deposition being conducted under CVD process conditions including a nitrogen atmosphere, or with post-deposition nitridation of the deposited tantalum/silicon material.

Tantalum silicon nitride films can also be formed in accordance with the invention by tantalum/silicon source compounds within the aforementioned general formula, where at least one of the R, and R' groups is a silicon-containing group, e.g., a silyl or substituted silyl group, and the TaSiN film is formed by CVD of material from the precursor in the presence of a nitrogen source material, e.g., a nitrogen atmosphere.

Specific examples of illustrative tantalum/silicon precursor compounds of the invention are set out below:

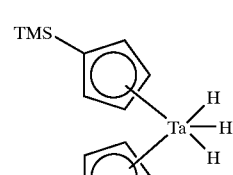

Formula (II)

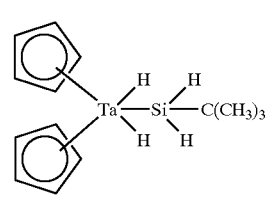

Formula (III)

In the compounds of the general formula (I) above, the $C_1$–$C_4$ alkyl substituents can be of any suitable type having such carbon numbers, with methyl, isopropyl, and tertiary butyl (t-butyl) being most preferred.

The substituent groups (R, and R') of the compounds of the invention can be tailored to provide a precursor compound having a specific desired volatilization and transport characteristic for the intended CVD application. The specific CVD process conditions can be widely varied in respective of temperature, pressure, flow rate of precursor and optional carrier gas or nitrogen source gas, and concentration (partial pressure) of precursor vapor in the CVD reactor chamber, etc., as is readily determinable without undue effort by those skilled in the art, based on the disclosure herein, by selective empirical variation of specific process conditions and analysis of the resulting tantalum-based material deposited on the substrate.

The compounds of formula (I) are readily synthesized from $(RCp)_2TaH_3$ for which one general synthetic scheme is set out below:

$$TaCl_5 + 2[(R)_nCp]Li + 3NaBH_4 \rightarrow [(R)_nCp]_2TaH_3 + Na/Li\ salts \quad (A)$$

wherein the reaction is conducted in tetrahydrofuran or other suitable aprotic solvent medium. Preferred process conditions include reaction under reflux conditions for suitable length of time, e.g., on the order of 4 hours, followed by hydrolysis with 2 equivalents of water, and reflux operation for a relatively short period of time, e.g., on the order of about 4 minutes.

A general synthetic scheme for compounds of formula (1) is set out below when addition of R' groups to the tantalum center are desired:

$$[(R)_nCp]_2TaH_3 + R'Li \rightarrow (RCp)_2TaH_2R' + \tfrac{1}{2}H_2 \quad (B)$$

which can be repeated in a stepwise manner until addition of same or differing R' groups is complete.

In the above synthesis reactions (A and B), the substituent groups (R, and R' groups) have the same definitions as those set forth in connection with formula (I) above.

Alternatively, the tantalum precursor of reaction (A) above can be used to form Ta/Si precursor compounds of the invention, by subsequent silylation reaction with suitable silane material. An example is the synthesis of cyclopentadienylsilyltantalum compounds of the formula $(R_nCp)_2TaH_2(RSiH_2)$ by reaction (C):

$$(RCp)_2TaH_3 + RSiH_3 \rightarrow (RCp)_2TaH_2(RSiH_2) + H_2 \quad (C)$$

Another example is the synthesis of $(RCp)_2TaH(R''SiH_2)_2$ by reaction (D):

$$(RCp)_2TaH_3 + 2R''SiH_3 \rightarrow (RCp)_2TaH(R''SiH_2)_2 + H_2 \quad (D)$$

The features and advantages of the invention are more fully shown by the following illustrative examples, wherein all parts and percentages are by weight, unless otherwise expressly stated.

EXAMPLE 1

Synthesis of $TMSCp_2TaH_3$

To 5.6 grams of freshly distilled trimethylsilylcyclopentadiene (TMSCp) in tetrahydrofuran (THF) was added 10% excess solution of BuLi in hexane. Upon completion of addition the mixture was stirred for 12 hours. The color of the reaction solution at the completion of the reaction was yellow. No solid formation was observed, due to the high solubility of the material in THF. To the freshly prepared solution of TMSCpLi (40 mmol) in THF and $NaBH_4$ (1.125 grams) was added slowly 3.5 grams of $TaCl_5$. On completion of addition, the mixture was refluxed for 4 hours following which 0.54 milliliter of degassed distilled water was added very slowly. After completion of the addition, the mixture was refluxed for an additional 5 minutes following which the volatiles were removed under vacuum. The compound was extracted with pentane and stored in the freezer. Brown crystals of $TMSCp_2TaH_3$ were obtained and washing these crystals with pentane gave very pure white crystals of the material (yield 35%).

Characterization

1H NMR ($C_6D_6$): 5.00 (m, 4H, Cp), 4.72 (m, 4H, Cp), 0.30 (s, TMS), −2.06 (t, 1H), −3.28 (d, 2H). STA thermal analysis of the compound yielded a melting point of 90° C. and a residue of 28.7% for $TMSCp_2TaH_3$.

Stability Study $TMSCp_2TaH_3$ does not decompose upon melting at 90° C. The compound can be sublimed intact at 74° C. to obtain pure white crystals.

Thus, in contrast to $Cp_2TaH_3$, the trimethylsilyl-substituted compound of this example has a low melting point, has high thermal stability and sublimes cleanly.

EXAMPLE 2

Synthesis of $Cp_2TaH_2(t-Bu)SiH_2$

To 0.5 gram of $Cp_2TaH_3$ in toluene was added 0.35 gram of $t-BuSiH_3$ in toluene. The reaction mixture was heated in a quartz reaction vessel at 135° C. for 6 days with three freeze-pump-thaw cycles each day. The solution was bright yellow in color. The solution was filtered and pumped to dryness. Pumping the solvent resulted in crystalline white material. 96% yield was achieved.

Characterization

1H NMR ($C_6D_6$): −4.73 (s, 2H, $TaH_2$), 1.37 (s, 9H, t-Bu), 4.57 (s, 10H, Cp), 4.81 (s, 2H, $SiH_2$). $^{13}$C NMR ($C_6D_6$): 30.42 (t-Bu), 85.81 (Cp).

Crystal Structure

The crystal structure of the product Ta/Si compound, $Cp_2TaH_2(t-Bu)SiH_2$, is shown in the ORTEP diagram of FIG. 1 hereof.

The Ta/Si compound of this example is usefully employed to form silicon-doped tantalum material layers as barrier layers on substrates in the fabrication of microelectronic devices and device precursor structures.

What is claimed is:

1. A compound of the formula:

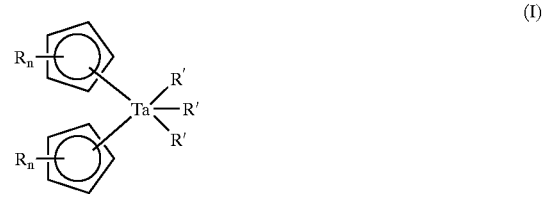

(I)

wherein:
n is an integer having a value of from 1 to 5;
each R can be the same or different and each is independently selected fr re the group consisting of D, H, $CH_3$, $C_2H_5$, i-$C_3H_7$, $C_4H_9$ and $Si(R'')_3$ wherein each R'' is independently selected from H and $C_1$–$C_4$ alkyl; and
each of R' can be the same or different and each is independently selected f in the group consisting of D, H, $C_1$–$C_4$ alkyl, and $Si(R'')_3$ wherein each R'' is independently selected from H and $C_1$–$C_4$ alkyl;
with the provisos that (i) each of the R groups and R' are not simultaneously all H, and (ii) when each of R' is H, and n is 1, both R groups are not simultaneously trimethylsilyl.

2. The compound of claim 1, wherein at least one of R, R' is $Si(R'')_3$ wherein each R'' is independently selected from H and $C_1$–$C_4$ alkyl.

3. The compound of claim 1, wherein at least one of R, R' is trimethysilyl.

4. The compound of claim 1, wherein n is 1 for each cyclopentadienyl ring.

5. The compound of claim 4, wherein R on each cyclopentadienyl ring is trimethylsilyl.

6. The compound of claim 1, wherein each of the R group and R are independently selected from H, methyl, isopropyl, t-butyl, trimethylsilyl, and t-butylsilyl.

7. The compound of claim 6, wherein at least one of the R groups and R' is trimethylsilyl.

8. The compound of claim 7, wherein n is 1 for each cyclopentadienyl ring.

9. The compound of claim 8, wherein R on each cyclopentadienyl ring is trimethylsilyl.

10. The compound of claim 1, wherein each of the R group and R' are independently selected from H and $Si(R'')_3$ wherein each R'' is independently selected from H and $C_1$–$C_4$ alkyl.

11. The compound of claim 10, wherein n is 1 for each cyclopentadienyl ring.

12. The compound of claim 11, wherein R on each cyclopentadienyl ring is trimethysilyl.

13. The compound of claim 11, wherein each R is H.

14. The compound of claim 13, wherein at least one of R' is Si(R'') wherein each R'' is independently selected from H and $C_1$–$C_4$ alkyl.

15. The compound of claim 14, wherein one of $R_1$, $R_2$ and $R_3$ is $Si(R'')_3$ wherein each R'' is independently selected from H and $C_1$–$C_4$ alkyl.

16. The compound of claim 15, wherein Si(R")$_3$ is alkylsilyl.

17. The compound of claim 16, wherein said alkylsilyl is t-butylsilyl.

18. A compound of the formula:

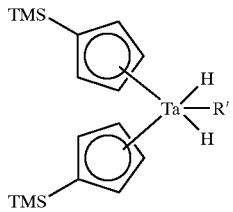

wherein TMS is trimethylsilyl and R' is selected from the group consisting of D, C$_1$–C$_4$ alkyl, and Si(R")$_3$ wherein each R" is independently selected from H and C$_1$–C$_4$ alkyl.

19. A compound of the formula:

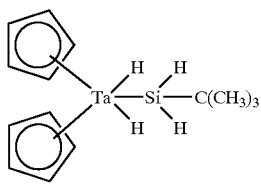

20. A method of forming a tantalum-containing material in a substrate, comprising contacting the substrate with a vapor of a tantalum precursor under chemical vapor deposition conditions, wherein said tantalum precursor comprises a compound of the formula:

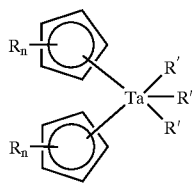

(I)

wherein:
n is an integer having a value of from 1 to 5;
each R can be the same or different and each is independently selected from the group consisting of D, H, CH$_3$, C$_2$H$_5$, i-C$_3$H$_7$, C$_4$H$_9$ and Si(R")$_3$ wherein each R" is independently selected from H and C$_1$–C$_4$ alkyl; and
each of R' can be the same or different and each is independently selected from the group consisting of D, H, C$_1$–C$_4$ alkyl, and Si(R")$_3$ wherein each R" is independently elected from H and C$_1$–C$_4$ alkyl.
with the provisios that (i) each of the R groups and R' are not simultaneously all H, and (ii) when each of R' is H, and n is 1, both R groups are not simultaneously trimethylsilyl.

21. The method of claim 20, wherein at least one of R' is Si(R")$_3$ wherein each R" is independently selected from H and C$_1$–C$_4$ alkyl.

22. The method of claim 20, wherein at least one of R,R' is trimethysilyl.

23. The method of claim 20, wherein n is 1 for each cyclopentadienyl ring.

24. The method of claim 23, wherein R on each cyclopentadienyl ring is trimethylsilyl.

25. The method of claim 20, wherein each of the R group and R' are independently selected from H, methyl, isopropyl, t-butyl, trimethylsilyl, and t-butylsilyl.

26. The method of claim 25, wherein at least one of the R group and R' is trimethylsilyl.

27. The method of claim 26, wherein n is 1 for each cyclopentadienyl ring.

28. The method of claim 27, wherein R on each cyclopentadienyl ring is trimethylsilyl.

29. The method of claim 20, wherein each of the R group and R' are independently selected from H and Si(R")$_3$ wherein each R" is independently selected from H and C$_1$–C$_4$ alkyl.

30. The method of claim 29, wherein n is 1 for each cyclopentadienyl ring.

31. The method of claim 30, wherein R on each cyclopentadienyl ring is trimethylsilyl.

32. The method of claim 30, wherein each R is H.

33. The method of claim 32, wherein at least one of R' is Si(R"), wherein each R" is independently selected from H and C$_1$–C$_4$ alkyl.

34. The method of claim 33, wherein one of R' is Si(R")$_3$ wherein each R" is independently selected from H and C$_1$–C$_4$ alkyl.

35. The method of claim 34, wherein Si(R")$_3$ is alkylsilyl.

36. The method of claim 35, wherein said alkylsilyl is t-butylsilyl.

37. The method of claim 20, wherein said precursor comprises:

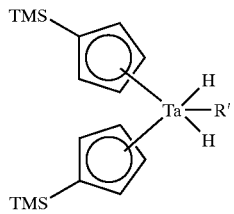

wherein TMS is trimethylsilyl and R' is selected from the group consisting of D, C$_1$–C$_4$ alkyl, and Si(R")$_3$ wherein each R" is independently selected from H and C$_1$–C$_4$ alkyl.

38. The method of claim 20, wherein said precursor comprises:

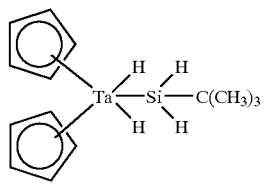

39. The method of claim 20, wherein the substrate comprises a semiconductor substrate.

40. The method of claim 20, wherein the substrate comprises a microelectronic device structure.

41. The method of claim 20, wherein the tantalum-containing material comprises a silicon-doped tantalum material.

42. The method of claim 20, wherein said chemical vapor deposition conditions comprise a nitrogen atmosphere.

43. The method of claim 20, wherein said tantalum-containing material comprises TaN.

44. The method of claim 43, wherein said chemical vapor deposition conditions comprise a nitrogen source for nitrogen in said TaN.

45. The method of claim 20, wherein said tantalum-containing material comprises TaSiN.

46. The method of claim 45, wherein said chemical vapor deposition conditions comprise a nitrogen source for nitrogen in said TaSiN.

47. The method of claim 20, wherein said substrate is a semiconductor substrate, and the tantalum-containing material comprises a material selected from the group consisting of TaN and TaSiN.

48. The method of claim 47, wherein the tantalum-containing material forms a diffusion barrier layer for copper metallization on said substrate.

49. The method of claim 48, wherein said copper metallization on said substrate has a line dimension of less than about 0.18 μm.

50. A method of synthesizing a cyclopentadienyl tantalum compound of the formula $[(R)_nCp]_2Ta(R')_3$ wherein:

n is an integer having a value of from 1 to 5;

each R can be the same or different and each is independently selected from the group consisting of D, H, $CH_3$, $C_2H_5$, $i-C_3H_7$, $C_4H_9$ and $Si(R'')_3$ wherein each R'' is independently selected from H and $C_1$–$C_4$ alkyl; and each of R' can be the same or different and each is independently selected in the group consisting of D, H, $C_1$–$C_4$ alkyl, and $Si(R'')_3$ wherein each R'' is independently elected from H and $C_1$–$C_4$ alkyl;

with the proviso that each of the R groups and R' are not simultaneously all H, said method comprising reacting tantalum pentachloride with a cyclopentadienyl-lithium compound of the formula $[(R)_nCp]_2Li$ in a 1:2 ratio and stepwise addition of sodium borohydride compound of the formula $NaBH(R')_3$ to yield said cyclopentadienyl tantalum compound according to the following formula:

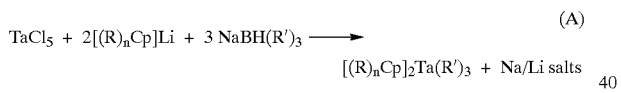
(A)

51. The method of claim 50, wherein said reacting step is conduct in a protic solvent medium.

52. The method of claim 51, wherein said protic solvent medium comprises tetrahydrofuran.

53. The method of claim 50, wherein said cyclopentadienyl tantalum compound is:

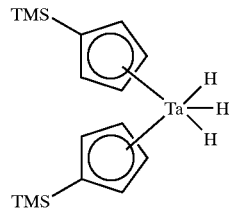

wherein TMS is trimethylsilyl.

54. The method of claim 50, further comprising reacting said cyclopentadienyl tantalum compound with a silane form a cyclopentadienylsilyltantalum compound.

55. The method of claim 54, wherein said silane comprises an alkylsiane.

56. The method of claim 55, wherein said alkylsilane comprises t-butysilane.

57. The method of claim 54, wherein said cyclopentadienylsilyltantalum compound comprises:

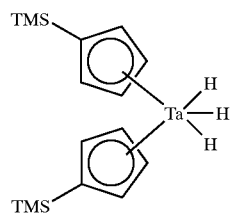

wherein TMS is trimethylsilyl.

58. The method of claim 54, wherein said cyclopentadienylsilyltantalum compound comprises:

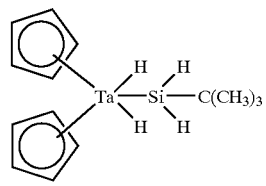

* * * * *